United States Patent [19]

Nakao et al.

[11] Patent Number: 5,347,991

[45] Date of Patent: Sep. 20, 1994

[54] ENDOSCOPE SUCTION TRAP AND ASSOCIATED METHOD

[76] Inventors: Naomi L. Nakao, 303 E. 57th St., New York, N.Y. 10022; Michael A. Nakao, 284 Hudson Ave., Albany, N.Y. 12210; John V. Mizzi, 30 Cramer Rd., R.F.D. #3, Poughkeepsie, N.Y. 12603

[21] Appl. No.: 963,846

[22] Filed: Oct. 20, 1992

[51] Int. Cl.⁵ .............................................. A61B 1/00
[52] U.S. Cl. .................................... 128/4; 604/319; 128/760
[58] Field of Search .................. 128/4, 6, 7, 8, 762, 128/760, 763, 765; 606/115, 127, 128, 114; 604/33, 35, 319, 320, 321, 313, 119, 902

[56] References Cited

U.S. PATENT DOCUMENTS

| | | | |
|---|---|---|---|
| 3,648,698 | 3/1972 | Doherty | 604/319 |
| 4,257,425 | 3/1981 | Ryan | 604/319 X |
| 4,334,538 | 6/1982 | Juhn | 604/119 X |
| 4,347,946 | 9/1982 | Nichols | 604/319 X |
| 4,643,197 | 2/1987 | Greene et al. | 604/319 X |
| 4,813,931 | 3/1989 | Hauze | 604/319 X |
| 5,084,034 | 1/1992 | Zanotti | 604/319 |
| 5,197,968 | 3/1993 | Clement | 606/115 |

*Primary Examiner*—Richard J. Apley
*Assistant Examiner*—Karen A. Jalbert
*Attorney, Agent, or Firm*—Davis Hoxie Faithfull & Hapgood

[57] ABSTRACT

A method for use in endoscopic investigations comprises the steps of providing an endoscopic insertion member with a suction line, inserting the endoscopic insertion member with the suction line into a patient, and visually inspecting organic tissues inside the patient with the endoscopic insertion member. To collect a fluid specimen, a port cover on the suction line is moved with respect to the suction line to open a port in the line. A specimen vial is coupled to the suction line at the opened port so that the suction line communicates with the vial. A vacuum is applied to the suction line to draw a fluid specimen into the vial. Subsequently, the vial is detached from the suction line, and the port cover moved back into position to again cover the port.

27 Claims, 2 Drawing Sheets

ENDOSCOPE SUCTION TRAP AND ASSOCIATED METHOD

BACKGROUND OF THE INVENTION

This invention relates to an endoscopic method and to an assembly utilizable in performing the method. More specifically, this invention relates to a suction trap for an endoscope and to an associated method.

In the conventional procedure for obtaining fluidic specimens during an endoscopic investigation, a vacuum line attached to the endoscopic insertion member must be detached from the endoscope. A trap is then inserted between the scope and the suction line. To implement the connection of the trap to the suction line, two short hoses with fittings are attached to the cap of a specimen trap battle. To return the endoscope to its normal trapless configuration, the two short hoses are detached and the vacuum line is then again directly attached to the endoscopic insertion member. To maintain the specimen trap bottle in an upright orientation during the specimen collection procedure, the bottle is generally secured to a rigid surface with adhesive tape. Upon a disconnection of the trap bottle from the suction line, the two hoses on the top of the bottle are inserted one inside the other to seal the specimen in the trap and to cover the ends of theses hoses which may have some liquid contamination.

In general, a nurse or other trained person is required to assist the endoscopist during the specimen collecting procedure. Because the endoscope is inserted into the patient, the physician cannot simply abandon the scope to manipulate vacuum hoses and traps. Any simplification in the procedure that would shorten the time for attachment or detachment would be advantageous since it would reduce patient discomfort.

OBJECTS OF THE INVENTION

An object of the present invention is to provide a simplified method for attaching and detaching a specimen trap to an endoscope suction line.

Another, more particular, object of the present invention is to provide such a method which could be implemented with one hand.

Another object of the present invention is to provide a device or assembly for use in carrying out the method.

A further object of the present invention is to provide such a device or assembly which is easy to use.

Yet another object of the present invention is to provide such a device or assembly which is easy to manufacture.

These and other objects of the present invention will be apparent from the drawings and detailed descriptions herein.

SUMMARY OF THE INVENTION

A method for use in endoscopic investigations comprises, in accordance with the present invention, the steps of (a) providing an endoscopic insertion member with a suction line, (b) inserting the endoscopic insertion member with the suction line into a patient, (c) visually inspecting organic tissues inside the patient with the endoscopic insertion member, (d) moving a port cover with respect to the suction line to open a port in the line, (e) coupling a specimen vial to the suction line at the opened port so that the suction line communicates with the vial, (f) applying a vacuum to the suction line to draw a fluid specimen into the vial, (g) detaching the vial from the suction line, and (h) moving the port cover back into position to again cover the port.

The coupling of the specimen vial to the suction line preferably includes the step of locking the vial to the suction line at the port. The locking may be implemented by inserting a snap lock male member into a snap lock female member, one such member being connected to the suction line and the other member being secured to the vial.

Where the vial is provided with a head portion having an inlet opening and an outlet opening, the application of suction to the suction line entails the step of drawing the fluid from a distal end portion of the suction line through the inlet opening into the vial.

Preferably, the inlet opening into the vial from the suction line is larger than the outlet opening from the vial into the line.

Pursuant to another feature of the present invention, the port cover is a sleeve slidably connected to the suction line. The steps of moving then include the step of sliding the sleeve relative in a longitudinal direction relative to the suction line.

Where the vial is provided with a cap attached to the vial via a flexible element, the method further comprises the steps of flipping the cap onto the vial and pressing the cap onto the vial.

Generally, the coupling of the vial to the suction line is performed subsequently to the insertion of the endoscopic insertion member into the patient. In addition, the specimen vial is generally removed from the suction line prior to the withdrawal of the endoscopic insertion member from the patient.

Pursuant to a further feature of the present invention, the method further comprises the step of rotating the vial with respect to the suction line after the coupling of the vial to the suction line. The rotation may be implemented automatically via a rotatable coupling.

Accordingly, a method for use in endoscopic investigations comprises, in accordance with a relatively specific conceptualization of the present invention, the steps of (i) providing an endoscopic insertion member with a suction line, (ii) connecting a port member into the suction line, (iii) sliding a port cover on the port member with respect to the suction line to open a recess in the port member, (iv) inserting a specimen container into the recess and attaching the container to the port member at the recess so that the suction line communicates with the container, (v) applying a vacuum to the suction line to draw a fluid specimen into the container, (vi) detaching the container from the port member and removing the container from the recess, and (vii) sliding the port cover back into position to again cover the recess.

According to another feature of the present invention, the steps of sliding, inserting and attaching, and detaching are performed manually with only one hand.

According to another feature of the present invention, the method further comprises the step of rotating the container with respect to the suction line after the step of inserting and attaching.

A suction trap assembly for use in endoscopic investigations comprises, in accordance with the present invention, a port member and a container member. The port member includes a body having an inlet coupling at one end and an outlet coupling at an opposite end, the inlet coupling and the outlet coupling being adapted for connection to segments of a suction line of an endoscope. The body is further formed with a recess, while a cover is movably connected to the body for removably covering the recess to enable fluid flow through the body from the inlet coupling to the outlet coupling. The specimen container member includes a vial, a head component secured to the vial, and a cap movably connected to the vial for removably covering the head component, thereby enabling closure of the vial upon a detachment of the container member from the port member. The head component of the container member includes means for defining an inlet opening and an outlet opening both communicating with the vial. The head component is received into the recess upon a shifting of the cover to uncover the recess. The suction trap assembly further comprises cooperating elements on the head component of the container member and the body of the port member for temporarily establishing a fluid flow path from the inlet coupling through the inlet opening, the vial, and the outlet opening to the outlet coupling while the head component is seated in the recess in the body of the port member.

In accordance with another feature of the present invention, the suction trap assembly further comprises locking elements on the head component and the body for releasably locking the container member to the port member. The locking elements may specifically include a snap lock male member on one of the head component and the body and a snap lock female member on the other of the head component and the body.

In accordance with a further feature of the present invention, the inlet coupling and the outlet coupling include rotatable ferrules for enabling a rotation of the port member relative to the suction line.

In accordance with an additional feature of the present invention, the cooperating elements include a partition web on the head component and means for forming a closure with the partition web upon a connection of the container member to the port member.

Preferably, the inlet opening in the head component of the container member is larger than the outlet opening.

Also, the head component is preferably formed with a funnel extending to the inlet opening.

In accordance with another feature of the present invention, the cap is connected to the head component via a flexible element.

In accordance with yet another feature of the present invention, the cover includes a sleeve slidably connected to the port member. The port member is advantageously provided with seals for forming a fluid tight seal upon a closure of the cover means over the recess.

A method in accordance with the present invention for attaching and detaching a specimen trap to an endoscope suction line represents a considerable simplification of the conventional procedure. The various steps in the method can be performed with one hand, whereby the examining physician or endoscopist may execute a specimen retrieval procedure without an assistant.

DETAILED DESCRIPTION

Figure 1:
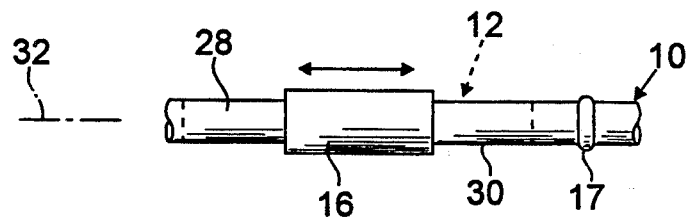
FIG. 1 is a side elevational view of a suction trap port member, on a reduced scale, in a closed configuration in an endoscope suction line, in accordance with the present invention.
Figure 2:
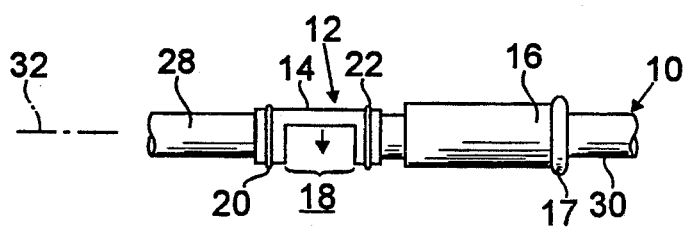
FIG. 2 is a side elevational view of the port member of FIG. 1 in an opened configuration, ready to receive a specimen container in accordance with the present invention.

As illustrated in FIG. 1 and 2, a suction trap assembly for connection in a vacuum or suction line 10 of an endoscope (not shown) comprises a port member 12 including a body portion 14 and a cover sleeve 16 slidably connected to the body portion. Body portion 14 is formed with a recess 18 (FIGS. 2, 4 and 5) which is covered by sleeve 16 in a normal, closed configuration of port member 12, illustrated in FIG. 1.

At the onset of a specimen collection procedure, sleeve 16 is moved longitudinaly along port member 12 until the sleeve engages a clamp 17. Clamp 17 functions as an arrest which prevents continued motion of sleeve 16.

As illustrated in FIGS. 2-5, body portion 14 of port member 12 is provided with a pair of 0-rings 20 and 22 on opposite sides of recess 18. 0-rings 20 and 22 are engaged by an inner surface of sleeve 16 in the closed configuration of port member 12 to seal the port member and thereby facilitate the conduction of liquid and/or gas through suction line 10.

Figure 3:
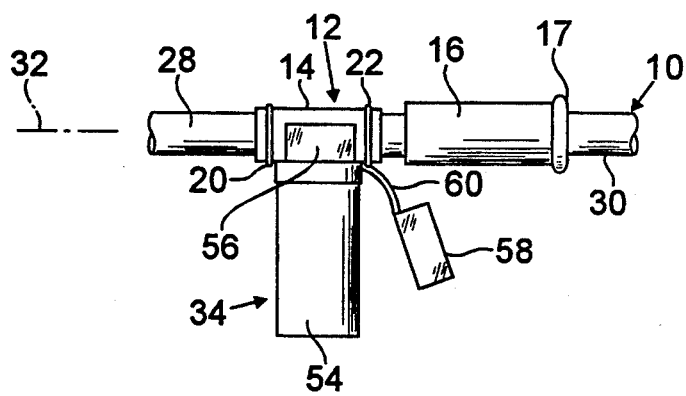
FIG. 3 is a side elevational view of the port member of FIG. 2 with an attached specimen container in accordance with the present invention.
Figure 4:
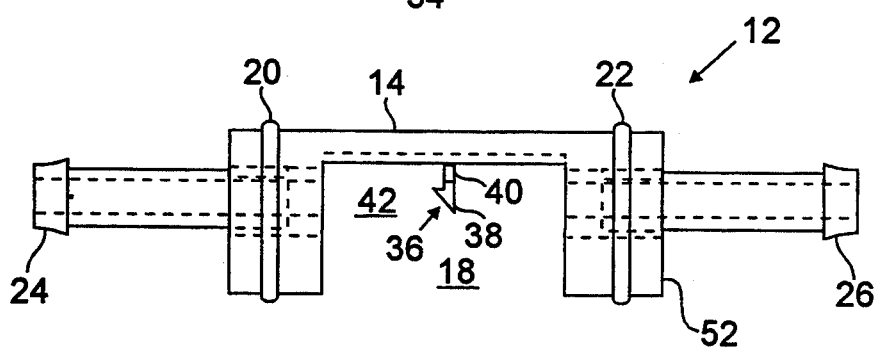
FIG. 4 is a side elevational view, on a larger scale, of a body portion of the suction trap port member of FIGS. 1-3.
Figure 5:
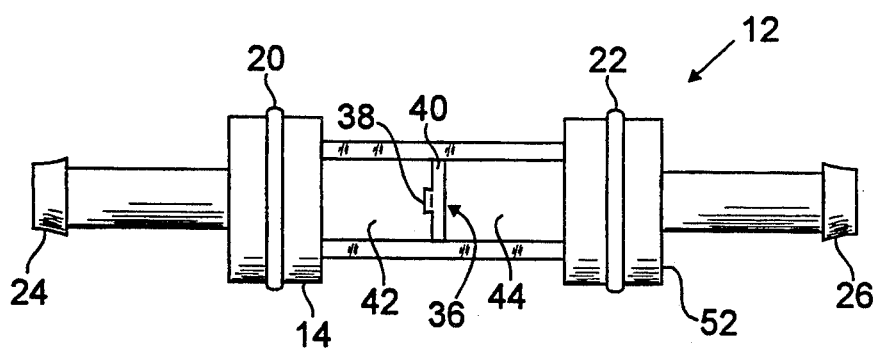
FIG. 5 is a bottom view, on a larger scale of the port member body portion of FIG. 4.

As shown in detail in FIGS. 4 and 5, body portion 14 of port member 12 is provided at opposite ends with an inlet coupling 24 and an outlet coupling 26 for connecting the port member to upstream and downstream segments 28 and 30 (FIGS. 1 and 2) of suction line 10. Inlet coupling 24 and outlet coupling 26 take the form of swivelable or rotatable ferrules which enable a rotation of port member 12 about a longitudinal axis 32 of suction line 10 upon attachment of a container member 34 (FIG. 3) to port member 12.

As shown in further detail in FIGS. 4 and 5, body portion 14 of port member 12 is provided in recess 18 with a snap lock element 36 including a hook 38 projecting from a shallow partition web 40. Partition web 40 separates an inner portion of recess 18 into two parts 42 and 44.

Figure 6:
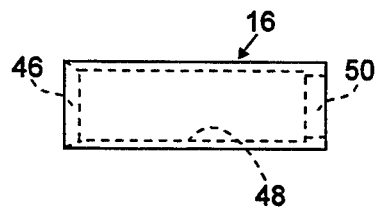
FIG. 6 is a side elevational view of a closure sleeve included in the port member of FIGS. 1-3.

As depicted in FIG. 6, sleeve 16 is a cylinder provided at one end with a beveled edge 46 for faciliating the sliding of the sleeve over 0-rings 20 and 22 during a closure stroke of the sleeve over recess 18. At an opposite end, sleeve 16 is formed along an inner surface 48 with an inwardly projecting annular flange 50 for defining a closure position of sleeve 16 with respect to body portion 14 of port member 12. Flange 50 abuts against 0-ring 22 or, alternatively, a shoulder 52 (FIGS. 4 and 5) of body portion 14.

Figure 7:
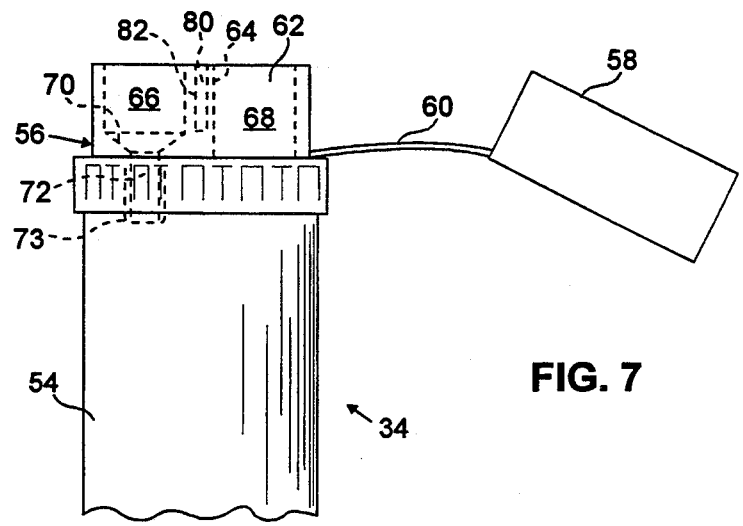
FIG. 7 is a side elevational view, on an enlarged scale, of the specimen container shown in FIG. 3.
Figure 8:
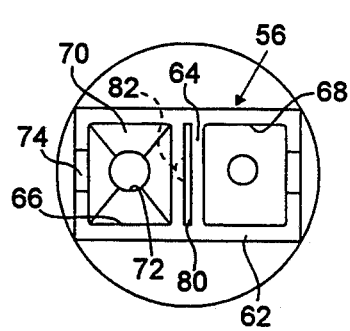
FIG. 8 is a top view of the container member of FIG. 7.
Figure 9:
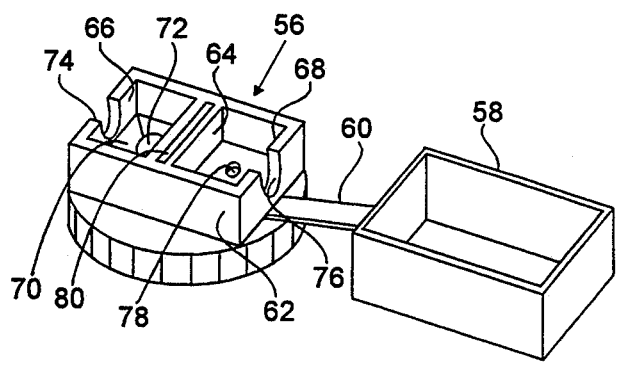
FIG. 9 is a perspective view of a head component of the container member of FIGS. 7 and 8.

As illustrated in FIGS. 3 and 7, specimen container member 34 includes a vial portion 54, a head component 56 secured to the vial, and a cap 58 movably connected to head component 56 and concomitantly to vial 54 via a flexible strap 60. As shown in FIGS. 7-9, head component 56 comprises an upwardly extending peripheral wall 62 and a partition web 64 extending between sides of wall 62 to form therewith a pair of antechambers 66 and 68. Antechamber 66 is provided in a lower region with a funnel surface 70 leading to an inlet opening 72. Funnel 70 channels incoming fluid through inlet opening 72 and a tubular extender element 73 into vial 54. The fluid enters antechamber 66 via an inlet aperture 74 formed as a slot in a side of wall 62. Antechamber 68 is also formed with such an aperture or slot 76 for enabling the evacuation of antechamber 68 via suction line segment 30 (FIGS. 1-3) and for concomitantly applying a vacuum to vial 54 during a specimen collection procedure. To that end, a lower region of antechamber 68 is provided with an outlet opening 78. Preferably, inlet opening 72 is larger than outlet opening 78.

As additionally shown in FIGS. 7-9, partition web 64 is provided with a recess or slot 80 for receiving partition web 40 on port member 12 (FIG. 4 and 5) upon an insertion of head component 56 into recess 18 during an initial stage of a specimen collection operation. At a lower end, slot 80 is provided with a transversely extending snap lock recess 82 for receiving snap lock element 36 in a snap lock fit upon insertion of head component 56 into recess 18.

Prior to the beginning of an endoscopic investigation, port member 12 is inserted into suction line 10 by connecting inlet and outlet couplings 24 and 26 to upstream and downstream suction line segments 28 and 30. Sleeve 16 is generally closed at this time. Upon subsequent insertion of an endoscopic insertion member (not shown) into a patient and upon visually inspecting internal organic tissues of the patient via optical components provided in the endoscopic insertion member, the endoscopist or an assistant slides sleeve 16 to open recess 18 and inserts head component 56 into recess 18 so that partition 40 is inserted into slot 80 of partition web 64 and so that male snap lock element 36 cooperates with female snap lock element or recess 82 to lock container member 34 to port member 12 at recess 18 (see FIG. 3). Upon attachment of container member 34 to port member 12, the port member swivels about axis 32 so that container member 34 is suspended essentially downwardly at all times. Suction is applied to line 10 so that a fluidic specimen is sucked through upstream suction line segment 28 to inlet coupling 24 and from the inlet side of port member 12 through antechamber 66 and inlet opening 72 into vial 54. A suction path continues from vial 54, through outlet opening 78 and antechamber 68 to coupling 26 and from there through downstream suction line segment 30.

Upon deposition of a specimen inside vial 54, suction may be terminated. Container member 34 is then removed from recess 18 of port member 12. The sides of body portion 14 may be squeezed to distort partition web 64 and facilitate the extraction of snap lock element 36 from snap lock recess 82.

Upon the separation of container member 34 from port member 12, cap 58 is snapped onto head component 56, thereby closing and sealing vial 54.

Sleeve 16 is moved longitudinally along body portion 14 to close recess 18 and return the suction trap assembly to the configuration disclosed in FIG. 1.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A method for use in endoscopic investigations, comprising the steps of:
   providing an endoscopic insertion member with a suction line;
   inserting said endoscopic insertion member with said suction line into a patient;
   visually inspecting organic tissues inside said patient with said endoscopic insertion member;
   moving a generally cylindrical port cover mounted externally on said suction line to open a port in said line;
   rigidly coupling a specimen vial to said suction line at the opened port so that said suction line communicates with said vial;
   applying a vacuum to said suction line to draw a fluid specimen into said vial;
   detaching said vial from said suction line; and
   moving said port cover back into position to again cover said port.

2. The method defined in claim 1 wherein said step of coupling includes the step of locking said vial to said suction line at said port.

3. The method defined in claim 2 wherein said step of locking includes the step of inserting a snap lock male member into a snap lock female member.

4. The method defined in claim 1 wherein said vial is provided with a head portion with an inlet opening and an outlet opening, said step of applying including the step of drawing said fluid from a distal end portion of said suction line through said inlet opening into said vial.

5. The method defined in claim 4 wherein said inlet opening is larger than said outlet opening.

6. The method defined in claim 1 wherein said port cover is a sleeve slidably connected to said suction line, and said steps of moving the port cover includes the step of sliding said sleeve in a longitudinal direction relative to said suction line.

7. The method defined in claim 1 wherein said vial is provided with a cap attached to said vial via a flexible element, further comprising the steps of flipping said cap onto said vial and pressing said cap onto said vial.

8. The method defined in claim 1 wherein said step of coupling is performed subsequently to said steps of inserting and inspecting.

9. The method defined in claim 1, further comprising the step of withdrawing said endoscopic insertion member from the patient, said steps of detaching and moving being performed prior to said step of withdrawing.

10. The method defined in claim 1, further comprising the step of rotating said vial with respect to said suction line after said step of coupling.

11. The method defined in claim 10 wherein said step of rotating is implemented automatically via a rotatable coupling.

12. A method for use in endoscopic investigations, comprising the steps of:
   providing an endoscopic insertion member with a suction line;

connecting a port member into said suction line;

sliding a port cover on said port member with respect to said suction line to open a recess in said port member;

inserting a specimen container into said recess and attaching said container to said port member at said recess so that said suction line communicates with said container;

applying a vacuum to said suction line to draw a fluid specimen into said container;

detaching said container from said port member and removing said container from said recess; and sliding said port cover back into position to again cover said recess.

13. The method defined in claim 12 wherein said steps of sliding, inserting and attaching, and detaching are performed with a single hand.

14. The method defined in claim 12, further comprising the step of rotating said container with respect to said suction line after said step of inserting and attaching.

15. The method defined in claim 12, further comprising the step of closing said container upon detachment thereof from said port member.

16. The method defined in claim 12, further comprising the step of continuing to apply suction to said suction line upon detachment of said container from said port member.

17. A suction trap assembly for use in endoscopic investigations, comprising:

a port member including:

a body having an inlet coupling at one end and an outlet coupling at an opposite end, said inlet coupling and said outlet coupling being adapted for connection to segments of a suction line of an endoscope, said body being formed with a recess; and cover means movably connected to said body for removably covering said recess to enable fluid flow through said body from said inlet coupling to said outlet coupling;

a specimen container member including:

a vial;

a head component secured to said vial, said head component including means for defining an inlet opening and an outlet opening both communicating with said vial, said head component being received into said recess upon a shifting of said cover means to uncover said recess; and cap means movably connected to said vial for removably covering said head component, thereby enabling closure of said vial upon a detachment of said container member from said port member; and cooperating means on said head component and said body for temporarily establishing a fluid flow path from said inlet coupling through said inlet opening, said vial, and said outlet opening to said outlet coupling while said head component is seated in said recess.

18. The assembly defined in claim 17, further comprising locking means on said head component and said body for releasably locking said container member to said port member.

19. The assembly defined in claim 18 wherein said locking means includes a snap lock male member on one of said head component and said body and a snap lock female member on the other of said head component and said body.

20. The assembly defined in claim 17 wherein said inlet coupling and said outlet coupling include means for enabling a rotation of said port member relative to said suction line.

21. The assembly defined in claim 20 wherein said means for enabling include rotatable ferrules.

22. The assembly defined in claim 17 wherein said cooperating means includes a partition web on said head component and means for forming a closure with said partition web upon a connection of said container member to said port member.

23. The assembly defined in claim 17 wherein said inlet opening is larger than said outlet opening.

24. The assembly defined in claim 17 wherein said head component is formed with a funnel extending to said inlet opening.

25. The assembly defined in claim 17 wherein said cap means includes a cap connected to said head component via a flexible element.

26. The assembly defined in claim 17 wherein said cover means includes a sleeve slidably connected to said port member.

27. The assembly defined in claim 17 wherein said port member is provided with sealing means for forming a fluid tight seal upon a closure of said cover means over said recess.

* * * * *